US00RE50170E

(19) United States
(12) Reissued Patent
Niazi

(10) Patent Number: US RE50,170 E
(45) Date of Reissued Patent: Oct. 15, 2024

(54) SUMMATION ANODAL PACING TO COMPLEMENT MULTISITE STIMULATION

(71) Applicant: Niazi Patent Holdings, LLC, River Hills, WI (US)

(72) Inventor: Imran K. Niazi, River Hills, WI (US)

(73) Assignee: Niazi Patent Holdings, LLC, River Hills, WI (US)

(21) Appl. No.: 17/366,327

(22) Filed: Jul. 2, 2021

Related U.S. Patent Documents

Reissue of:
(64) Patent No.: 8,838,237
Issued: Sep. 16, 2014
Appl. No.: 13/053,965
Filed: Mar. 22, 2011

U.S. Applications:
(63) Continuation-in-part of application No. 12/899,244, filed on Oct. 6, 2010, now abandoned.

(60) Provisional application No. 61/272,563, filed on Oct. 6, 2009.

(51) Int. Cl.
*A61N 1/362* (2006.01)
*A61N 1/05* (2006.01)

(52) U.S. Cl.
CPC ..... *A61N 1/3622* (2013.01); *A61N 1/0587* (2013.01)

(58) Field of Classification Search
CPC .... A61N 1/368; A61N 1/0416; A61N 1/3622; A61N 1/371
See application file for complete search history.

(56) References Cited

U.S. PATENT DOCUMENTS

| | | | | |
|---|---|---|---|---|
| 3,915,174 | A | 10/1975 | Preston | |
| 5,800,465 | A | 9/1998 | Thompson et al. | |
| 6,341,234 | B1 | 1/2002 | Thong et al. | |
| 7,177,680 | B2 | 2/2007 | Sharma et al. | |
| 7,389,140 | B1 | 6/2008 | Kroll | |
| 8,126,546 | B2 | 2/2012 | Williamson | |
| 9,415,226 | B1 * | 8/2016 | Snell | A61N 1/36843 |
| 2008/0294211 | A1 | 11/2008 | Moffitt | |
| 2009/0005845 | A1 | 1/2009 | David et al. | |
| 2009/0198296 | A1 | 8/2009 | Sanghera et al. | |
| 2009/0240298 | A1 | 9/2009 | Lian et al. | |
| 2010/0121396 | A1 | 5/2010 | Gill et al. | A61N 1/3712 607/17 |
| 2010/0121404 | A1 * | 5/2010 | Bjorling | A61N 1/3712 607/28 |

(Continued)

*Primary Examiner* — Matthew J Kasztejna
(74) *Attorney, Agent, or Firm* — Boyle Fredrickson S.C.

(57) ABSTRACT

A device and method for cardiac pacing is disclosed in which anodal pacing of the left ventricle is provided. Anodal pacing occurs when an anodal surface area is sufficiently small to create an area of hyper-polarization of the myocardial cell membrane. This creates a virtual cathode at a location remote from the anode. The virtual cathode results in depolarization of the heart in a manner similar to the virtual cathode at the true fixed cathode. In addition a device and method for summation anodal pacing is provided in which one anode is common between two or more cathodes. This results in hyperpolarization of a larger segment of the myocardium as compared to non-summation anodal pacing and thereby forms a larger virtual electrode to enable capture of localized, discrete cardiac structures such as the bundle of His or the very proximal portions of the right and left bundles.

32 Claims, 8 Drawing Sheets

(56) References Cited

U.S. PATENT DOCUMENTS

| | | | | |
|---|---|---|---|---|
| 2010/0125315 | A1 | 5/2010 | Parramon et al. | |
| 2010/0174336 | A1* | 7/2010 | Stein | 607/23 |

* cited by examiner

SUMMATION ANODAL PACING TO COMPLEMENT MULTISITE STIMULATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a continuation-in-part of and claims the benefit of the filing date of co-pending U.S. patent application Ser. No. 12/899,244 filed on Oct. 6, 2010 and entitled "Summation Anodal Pacing to Complement Multisite Stimulation," which claims priority from U.S. Provisional Patent Application Ser. No. 61/272,563, filed on Oct. 6, 2009, the entire contents of which are hereby expressly incorporated by reference into the present application.

BACKGROUND OF THE INVENTION

1. Field of the Invention

This invention pertains to the medical field and, more particularly, pertains to uniquely designed pacing circuits to allow stimulation of multiple areas of the heart using anodal as well as cathode current.

2. Discussion of the Related Art

Traditional pacing of heart chambers is accomplished by delivering electrical current to cardiac tissue at a cathode of a pacing lead. An anode is provided as either a pacemaker/defibrillator casing (unipolar pacing) or as a separate anode positioned on the pacing lead with a large surface area to prevent anodal capture (bipolar pacing).

Cardiac pacing has been used for at least 50 years to sustain the heart rhythm in patients with slow or absent innate electrical activation. Conventional pacing uses cathodal capture to excite heart muscle. By delivering a current impulse (electrons) via a conductor, a segment of the myocardial cell membrane is rendered more negative such that the threshold potential is reached. This initiates an action potential, which is propagated to adjacent myocardial cells such that eventually the entire heart muscle is depolarized. More recently, pacing of the left ventricle has been used to synchronize the heart in patients with left bundle branch block, thereby reducing instances of heart failure.

Capture of myocardium depends upon current density; a smaller electrode will provide greater current density with the same current than a larger electrode. Traditional theory holds that a certain minimal area of the heart must be captured to allow propagation of the impulse through the heart muscle Capture also depends upon the ease with which current is transferred to underlying viable myocardial tissue. Diseased tissue or poor connection between electrode and myocardium will increase pacing thresholds. Thus, a small electrode surface area and good contact with viable underlying myocardial tissue is required to achieve capture with minimal current expenditure.

Recent epi-fluorescence membrane studies have demonstrated that the phenomenon of myocardial capture is much more complicated than previously thought. It appears application of current at the cathode, results in the formation of a "virtual cathode" of "dog bone" shape oriented at a 45 degree angle. Stimulation and propagation depend upon the virtual cathode exciting viable myocardial tissue.

Heretofore, anodal capture has been considered undesirable on largely theoretical grounds. In particular, it has been theorized that anodal current may be pro-arrhythmic and may also cause mechanical deterioration of the electrode tip. These theories have now been largely discredited. It has been shown that in left ventricular (LV) pacing, unintended anodal capture occurs frequently and may even have salutary hemodynamic effects.

Anodal pacing occurs when the current introduced to the heart at the cathode returns to the pacemaker circuit via the anode. When the anodal surface area is sufficiently small, this creates an area of hyper-polarization of the myocardial cell membrane. In turn, this sets up a "virtual cathode" remote from the anode. The virtual cathode results in depolarization of the heart in a manner similar to the virtual cathode at the true fixed cathode.

There are at least two advantages to anodal pacing. First, if the virtual cathode lies in an area of healthy myocardium, the anodal threshold may actually be lower than the true cathodal threshold, especially if the cathode lies in an area of diseased myocardium or has a poor connection to the underlying myocardium. Second, if a considerable distance separates the anode and cathode, the area of the myocardium that can be stimulated will be increased by the formation of virtual cathodes. This may have advantages in allowing rapid depolarization of the myocardium; it may also allow capture of a particular small, specifically located structure, such as the His bundle.

The need therefore exists to provide a cardiac pacing apparatus and method including electrical circuits configured to allow for anodal capture.

SUMMARY OF THE INVENTION

In accordance with a first aspect of the invention, a pacing device is provided for anodal pacing of one or more electrodes in a bipolar or multipolar lead for the left ventricle (LV). In particular, a pacing-enhanced circuit for left-ventricular stimulation may be provided.

In a second aspect of the invention, anodal pacing is utilized to capture the His bundle or the very proximal right and left bundles, i.e., His or Para-his pacing. This may be carried out using a bipolar or multipolar lead designed such that multiple poles are in contact with the tricuspid annuls in close proximity to the bundle of His by way of the virtual cathode created by the fixed cathode as well as the virtual cathode created by the anode.

In yet another aspect of the invention, anodal pacing may be used in patients requiring bi-atrial pacing. In still another aspect of the invention, the left atrial lead may serve as the anode for the right ventricular pacing lead.

Various other features, embodiments and alternatives of the present invention will be made apparent from the following detailed description taken together with the drawings. It should be understood, however, that the detailed description and specific examples, while indicating preferred embodiments of the invention, are given by way of illustration and not limitation. Many changes and modifications could be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings, in which like reference numerals represent like parts throughout, and in which.

DETAILED DESCRIPTION OF THE PREFERRED EMBODIMENTS

In cardiac pacing, if a single electrode of appropriate size serves as the anode for a single cathode delivering an amount of current represented as X, then an amount of current represented as Y will be delivered to the anode. Summation anodal pacing is a method of cardiac pacing in which if the same anode serves as a common anode for two cathodes and each cathode is delivering an amount of current represented as X, then 2Y current will be delivered to the anode. This results in the hyperpolarization of a larger segment of the myocardium adjacent the anode, and consequently, the creation of a larger virtual electrode. This is likely to reduce the anodal pacing threshold. Further, the larger the virtual electrode, the more likely it is to capture a localized, discrete structure within the heart such as the Bundle of His or the very proximal portions of the right and left bundles.

Figure 1:
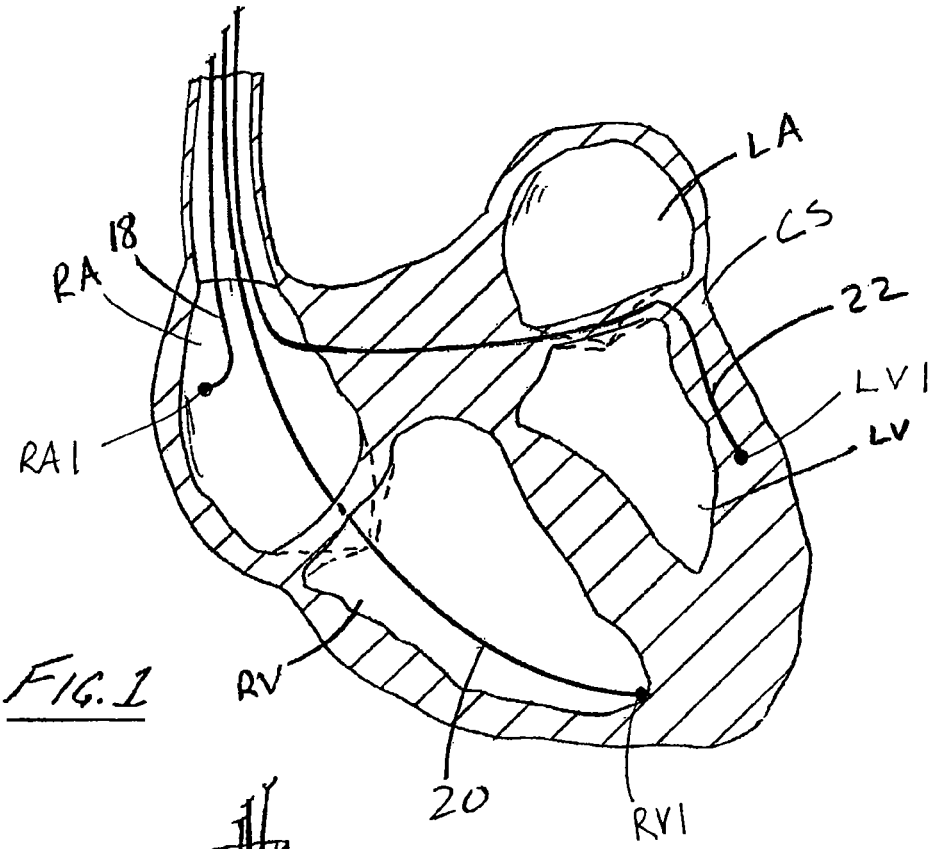
FIG. 1 is a schematic view of leads of a device, e.g., a biventricular pacemaker or defibrillator, coupled to a heart.
Figure 8:
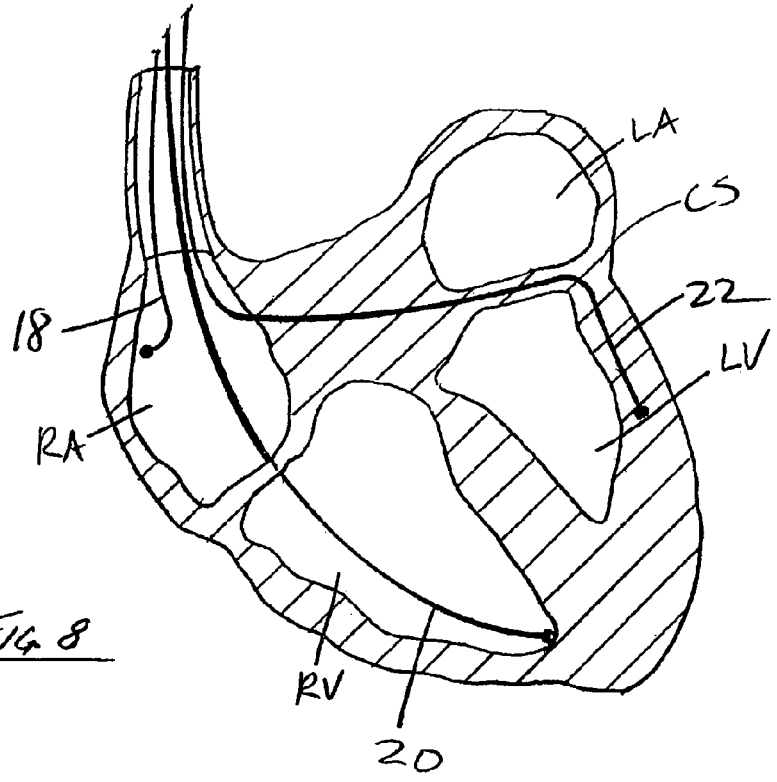
FIG. 8 is a schematic view of the leads similar to that of FIGS. 1 and 2 and showing a bipolar lead in the RA, a bipolar lead in the RV and a bipolar or multipolar lead in the LV.
Figure 15:
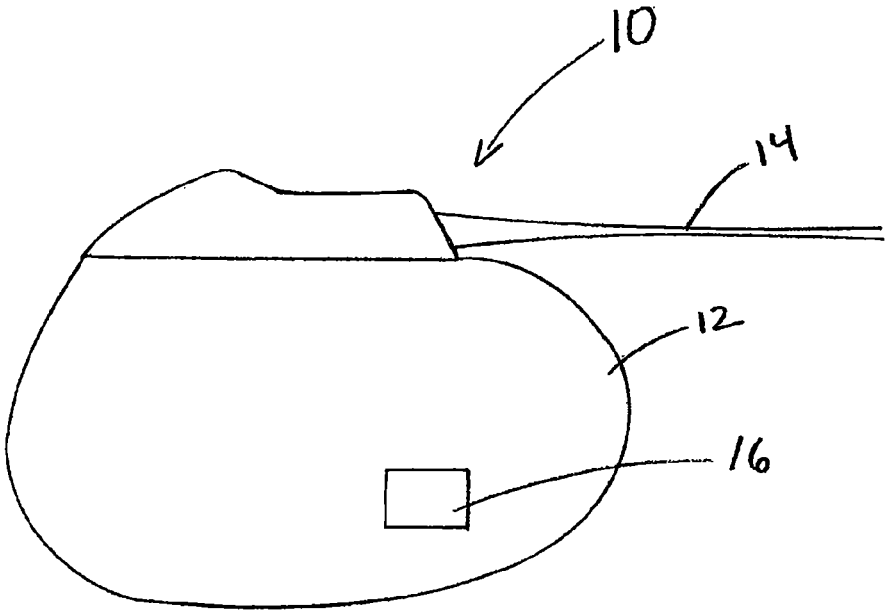
FIG. 15 is a schematic view of the device according to the invention in which the device is a pacemaker.

Referring now to the drawings, and initially FIG. 1, a schematic illustration of a heart is provided. The heart includes four chambers, namely: a right atrium RA, left atrium LA, right ventricle RV, and left ventricle LV. The coronary sinus CS is shown in the groove between the left atrium and left ventricle on the posterior surface of the heart. Referring now to FIGS. 1 and 8, the positions of a number of leads of a device 10 (see FIG. 15) according to the invention are shown. The device 10 may be, for example, a biventricular pacemaker or a defibrillator. Device 10 includes a housing 12 for carrying and protecting the circuitry of the device 10. Housing 12 is configured for mounting within a cavity of a patient as is generally understood. One or more lead wires 14 are operably coupled with device 10 and extend from the housing 12. Device 10 may be powered by a battery 16 of the kind generally known in the art. The embodiment of the invention illustrated in FIGS. 1 and 8 shows a bipolar lead 18 in the RA, a bipolar lead 20 in the RV, and a bipolar or multipolar lead 22 in the LV are shown.

A pacing enhanced circuit for left ventricular stimulation according to an embodiment of the present invention may include a biventricular pacemaker having a battery capable of powering at least three pacing circuits. The three pacing circuits are provided to pace the RA, RV endocardium and the LV epicardium via a branch of the coronary vein. In addition, device 10 may include one or more sensing circuits that may sense intrinsic electrical activity from any or all of the three locations.

The RA pacing circuit usually incorporates a bipolar lead in which a tip electrode serves as the cathode, and a proximal ring electrode serves as the anode. Capture of the myocardium may occur from the cathode as the electrical current (electrons) generated by the cathode by the pacing circuit depolarizes the cell membranes of a critical mass of myocardium. A local action potential is thereby initiated that subsequently propagates through the myocardium. There are several factors which determine whether successful "capture" of the myocardium occurs. The factors include the (i) amount of the current applied, (ii) duration of application, (iii) lead and tissue impedance, and (iv) electrode surface area. These factors serve to define a resultant current density, and the current density at the electrode tissue interface determines successful depolarization of the cell membranes and propagation of the action potential.

Figure 2:
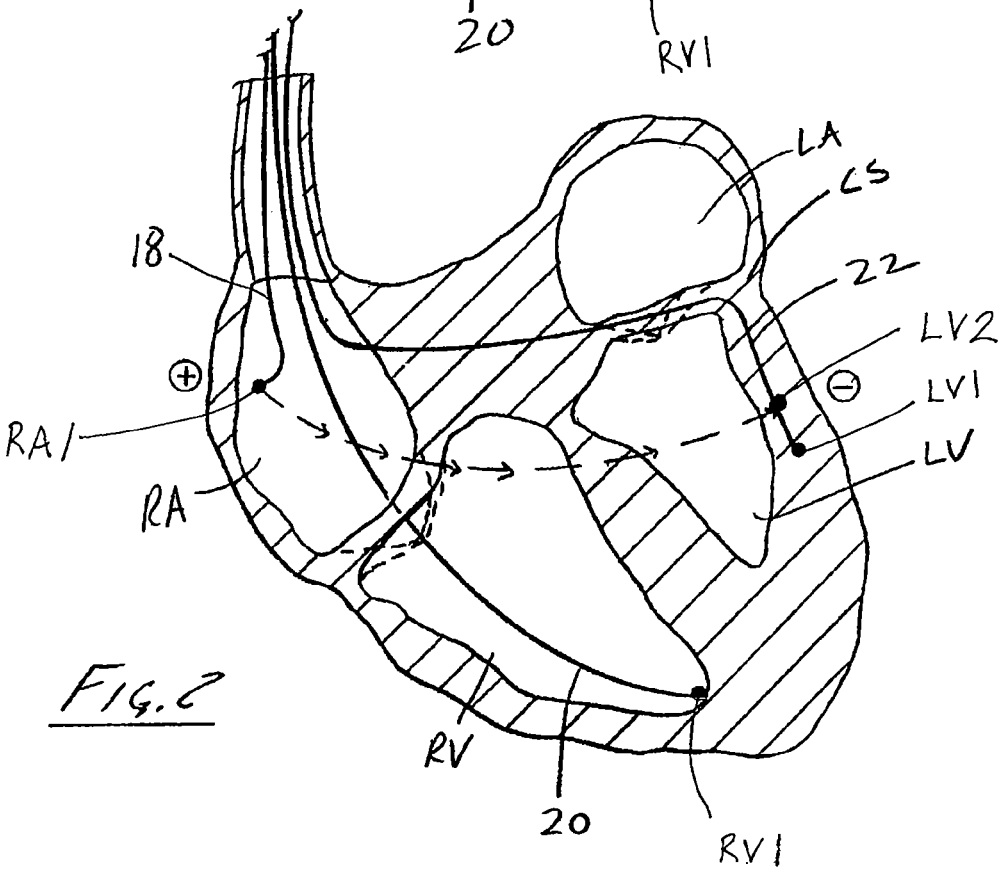
FIG. 2 is a schematic view of the leads of the device of FIG. 1 in which a sub-threshold stimulus is applied and preconditions a left ventricular (LV) anode, which serves as the anode for the right atrium (RA)

Referring now to FIG. 2, the effect of a sub-threshold stimulus on the LV anode is shown. In particular, the sub-threshold stimulus preconditions the LV anode and the LV anode serves as the anode for the RA. This is schematically demonstrated in FIG. 2 by way of the presence of a number of arrows demonstrating the current flow from the RA to the LV, wherein current emanates from electrode RA1 and flows into electrode LV2.

If the right atrial pacing circuit is configured such that the anode is one of the (selected) electrodes of the LV lead, anodal stimulation can occur. Normally, this is not desirable as the LV stimulation should occur at least 70 msec after the atrial stimulus. However, if the right atrial cathodal stimulus is relatively small, sub-threshold stimulation of the chosen LV electrode will occur. This has been shown to decrease the threshold for a subsequent LV anodal stimulus, as demonstrated by, e.g. FIG. 2.

Figure 12:
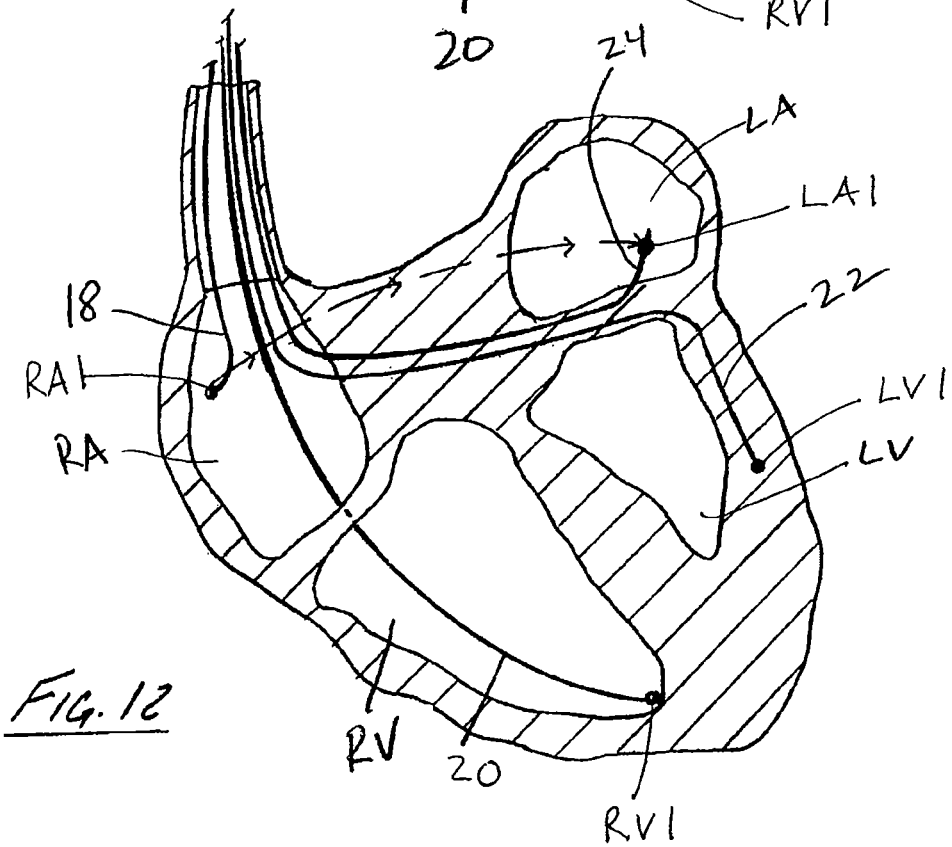
FIG. 12 is a schematic view of the leads of the device of the invention coupled to the heart and showing the LA lead as the anode for the RA channel.

With respect to biatrial pacing in a CRT device, it is possible to pace the left atrium via leads introduced into the proximal coronary sinus and into the obtuse vein of Marshall or by direct fixation onto the epicardial surface of the LA. In particular, a left atrial lead 24 may be provided. It is theorized that this may improve LA-LV synchrony. The LA may be paced using the RA channel in a unipolar fashion; the LA electrode would then serve as the cathode; while the RA electrode serves as the anode as shown in FIG. 12.

Figure 13:
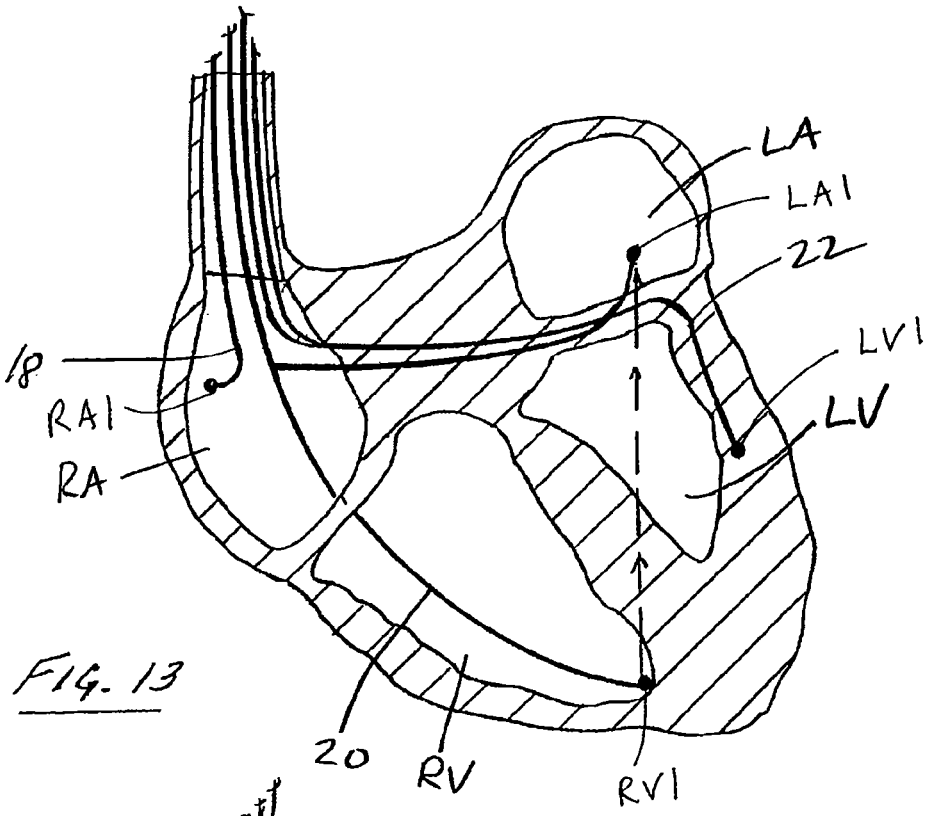
FIG. 13 is a schematic view showing the leads o coupled to the heart and showing the LA lead as anode for the RV channel.
Figure 14:
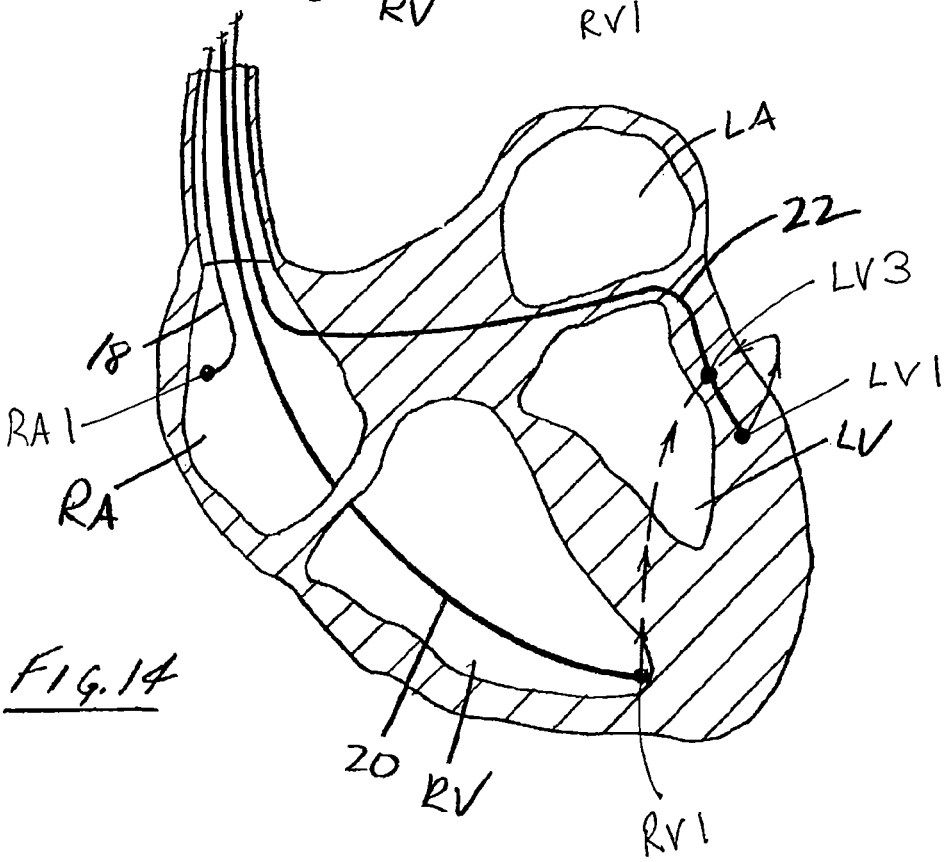
FIG. 14 is a schematic view showing the leads o coupled to the heart and showing the LV lead as the anode for the RV channel.

With respect to FIG. 13, in certain circumstances, it may be desirable to pace the LA and RA at different times with each timed to its respective ventricle. This would require an additional channel, i.e., the LA channel, in the pacing CRT device. As there is a delay of at least 70 milliseconds between RA pacing and RV pacing, it is conceivable that the RV channel could be used to anodally pace the LA as there is prolonged intra-atrial conduction time when the RA is paced from the RA appendage. The average time delay in such situations is approximately 70 milliseconds. Of course alternative delay times are within the scope of the present invention.

In pacemakers, the RV pacing circuit is usually connected to a bipolar lead with the tip electrode serving as the cathode. The proximal electrode on the RV lead usually functions as the anode. As in atrial circuits, the size of the proximal electrode is at least 7 times that of the tip electrode to minimize the chances of anodal capture of the right ventricle. Anodal capture of the right ventricle has traditionally been thought to be deleterious to the patient, and this pacing modality is avoided in the ventricles by increasing the size of the anode to reduce current density and avoid anodal capture.

In one embodiment, a selected electrode of the multipolar LV lead would serve as the anode. Thus, anodal capture at the selected LV electrode could be achieved along with cathodal capture from another selected LV pole via the LV channel. If the RV and LV are paced simultaneously, such an arrangement would have the advantage of allowing anodal stimulation of an additional LV electrode without expending additional battery energy. This would be possible if the anodal threshold in the selected LV electrode were to be less than the anodal current delivered by the RV channel.

Referring now to FIGS. 3-6, in some situations, the selected LV electrode may not have an anodal threshold appropriate for anodal stimulation via the RV channel. In that case, another LV electrode could be used as the LV anode, or the selected anode could serve as the common anode of the RV cathode and the LV cathode(s), which would increase current density and allow anodal capture at the selected LV electrode without expending additional battery energy.

Figure 3:
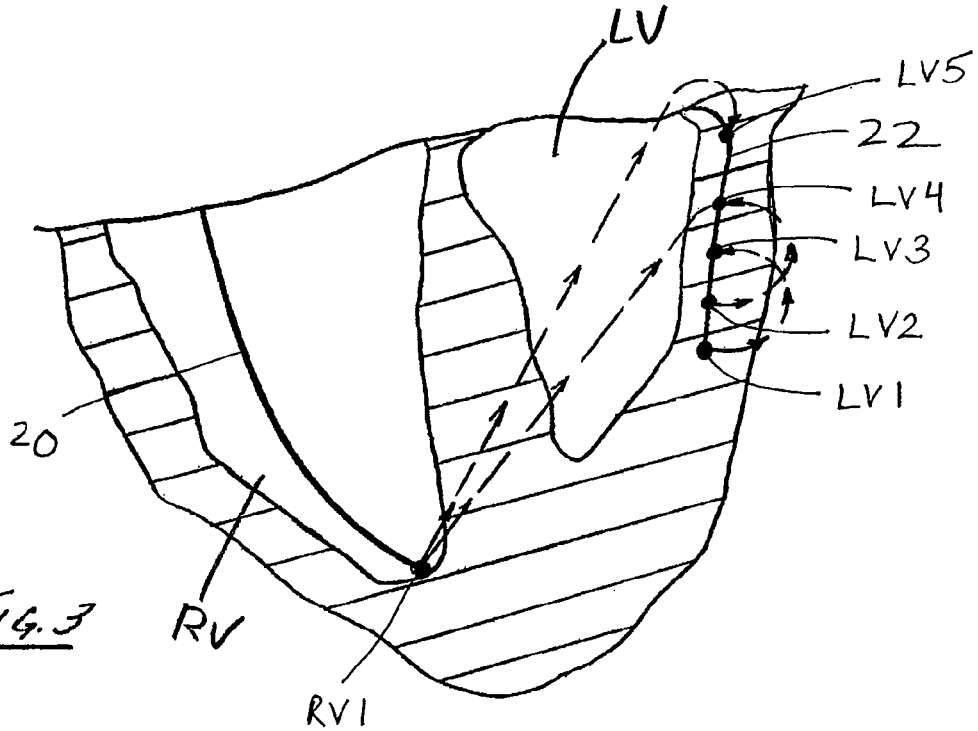
FIG. 3 is a schematic view of the leads of FIGS. 1 and 2 and showing the leads coupled to the right ventricle (RV) and left ventricle and demonstrating the concept of summation anodal pacing.

Referring now to FIG. 3 in particular, the LV multipolar lead 22 has five electrodes, which may be denoted as electrodes 1-5 (LV1, LV2, LV3, LV4, and LV5) starting at the tip with LV1 and moving proximally therefrom in succession. In this configuration, LV1 and LV2 are paced as cathodes through the LV channel. The RV tip electrode (RV1) is paced as the cathode. LV3 serves as the anode for the LV1, LV4 serves as the common anode for the RV cathode and the LV2 cathode, and LV5 serves as the anode for the RV cathode. A sixth electrode LV6 (not shown) may be provided and serve as a cathode, and a seventh electrode LV7 (not shown) may be provided and serve as the common anode for RV cathode as well as LV6.

Figure 4:
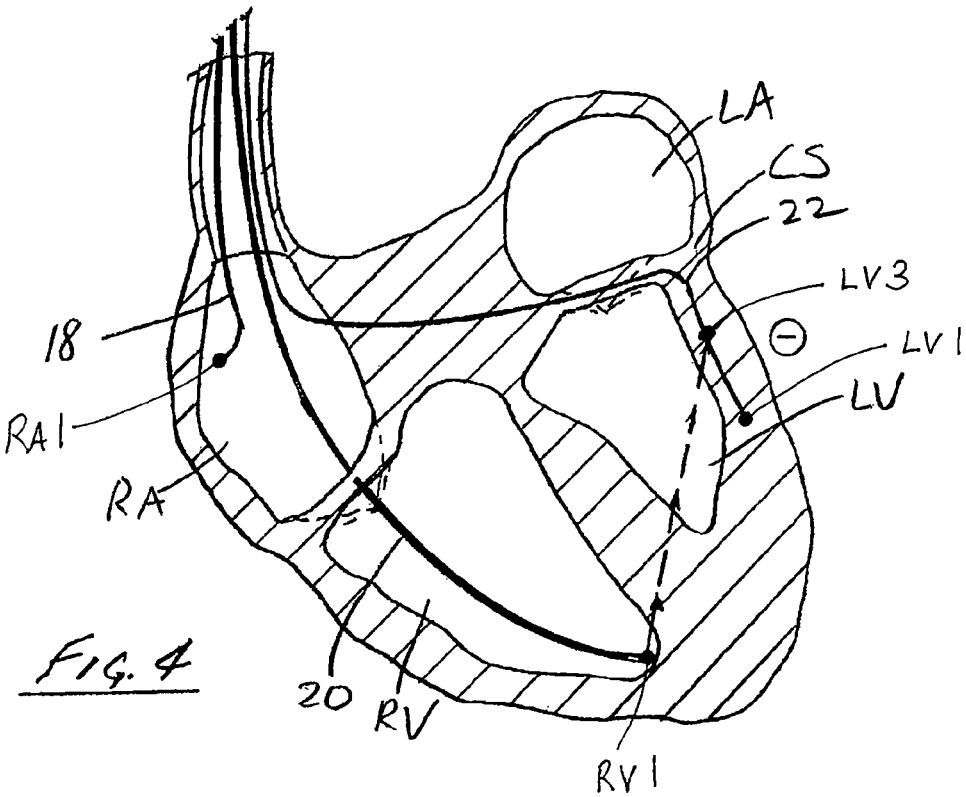
FIG. 4 is a schematic view of the leads of FIGS. 1 and 2 and demonstrating the concept of LV anodal summation as a byproduct of RV stimulation.

Turning to FIG. 4, LV anodal stimulation is demonstrated as a byproduct of RV stimulation. In particular, a multipolar lead is positioned in the LV, and LV3 thereof serves as the anode for the RV channel cathode. With respect to FIG. 5, LV3 multipolar lead 22 serves as the common anode for the RV cathode, LV1 cathode, and LV6 cathode.

Figure 6:
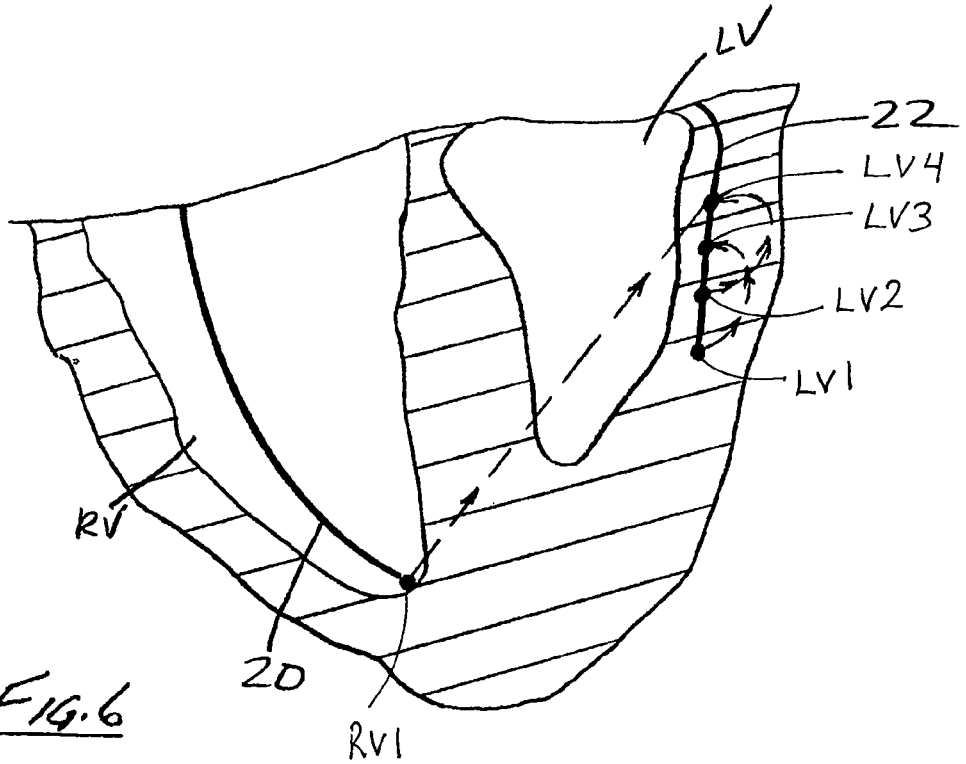
FIG. 6 is a partial schematic view of the leads of FIGS. 1 and 2, coupled to the right and left ventricles of the heart and demonstrating the concept of summation anodal pacing in a quadripolar LV lead.
Figure 7:
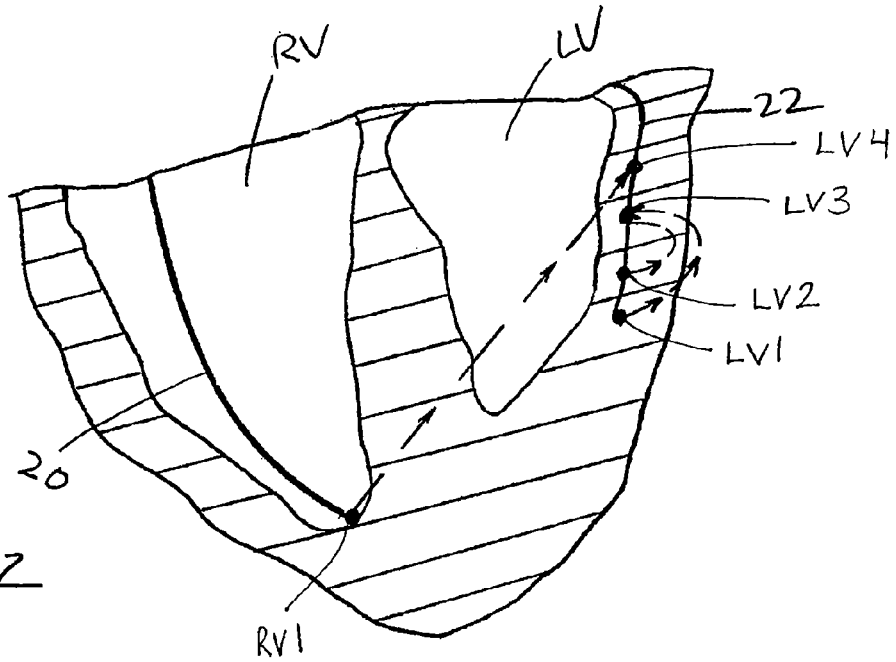
FIG. 7 is a partial schematic view like that of FIG. 6 and demonstrating the concept of summation anodal pacing a quadripolar LV lead.

Turning now to FIGS. 6 and 7, there are situations when some electrodes of a multipolar lead need to be stimulated earlier or later than the RV cathode. For example, in a quadripolar lead with widely spaced electrodes pacing different areas of the LV, it may be preferential to stimulate some electrodes earlier than others. In this situation, using LV offset, cathodal stimulation of electrodes 1 and 2 could be performed earlier than anodal stimulation of, e.g., LV 3 or LV4. Either or both of the LV3 and LV4 could be stimulated anodally using the RV channel.

Figure 5:
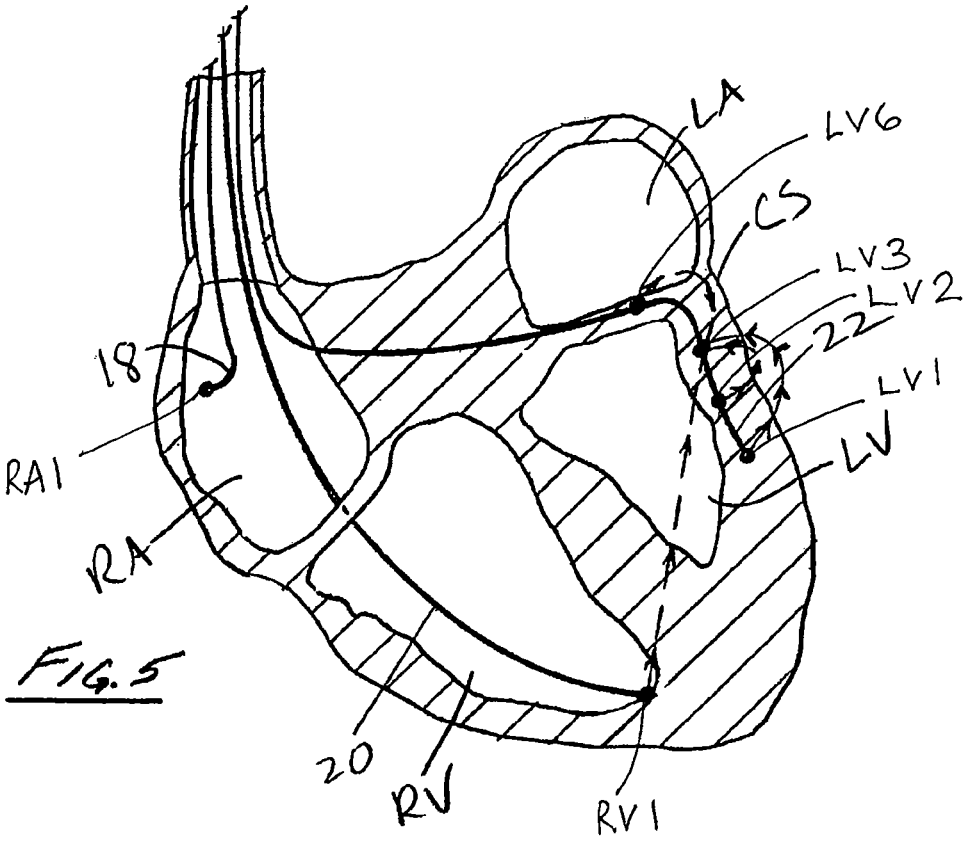
FIG. 5 is a schematic view of the leads of FIGS. 1 and 2, coupled to the heart and demonstrating the concept of summation anodal pacing in which an electrode of the LV multipolar lead serves as a common anode for the RV cathode, LV1 cathode and LV6 cathode.

With reference again to FIG. 8, the LV pacing channel may be used to simulate one or more cathodes in a multipolar lead, stimulate other LV electrodes by making them the anodes for the LV cathodes as in FIG. 5, and some LV electrodes may be stimulated by making them common anodes between the RV and LV channels as shown in FIG. 6.

Figure 9:
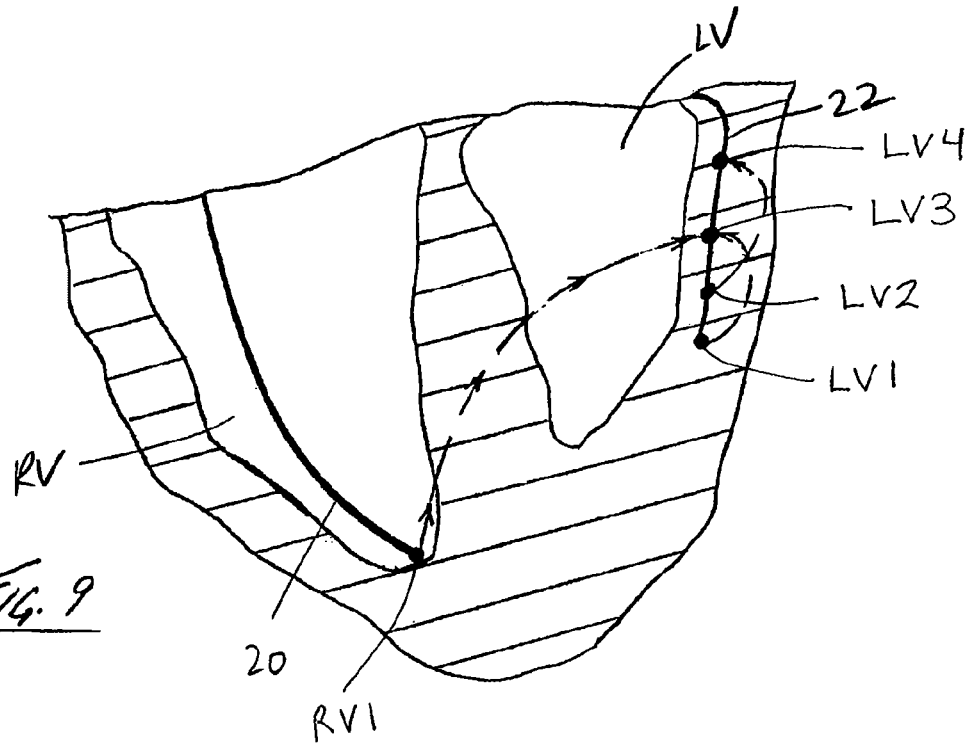
FIG. 9 is a partial schematic view showing the coupling of leads to the LV and RV of the heart and demonstrating the manner in which RV and LV channels in a biventricular pacing device may be configured to stimulate multiple electrodes on the LV lead.

In patients with atrial fibrillations (AF), the atrial channel is not used. As is demonstrated in FIG. 9, the atrial channel may be connected to another LV lead (multi-lead, multi-site LV stimulation, or MMLVS). This allows the opportunity for summation anodal pacing of multiple sites using two multipolar leads. In particular, the atrial, RV, and LV channels in a biventricular pacing device may be configured to stimulate multiple electrodes on the LV lead. LV1 serves as the cathode for the LV channel, LV2 serves as a cathode for the RA channel, and LV3 serves as a common anode, i.e., anodal summation capturing anode for LV1 and RV channels. Meanwhile, LV4 serves as the anode for LV2 (RA channel).

Figure 10:
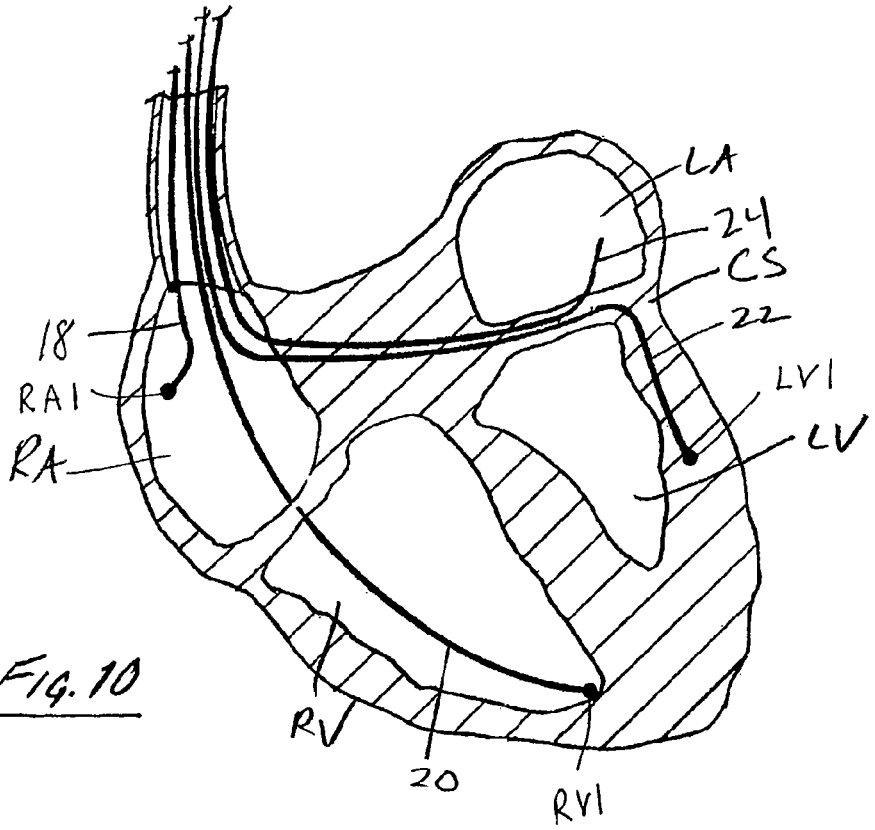
FIG. 10 is a schematic view showing the coupling of leads to the heart and showing the leads in the RA, RV, LV and left atrium (LA) introduced through the vein of Marshall.
Figure 11:
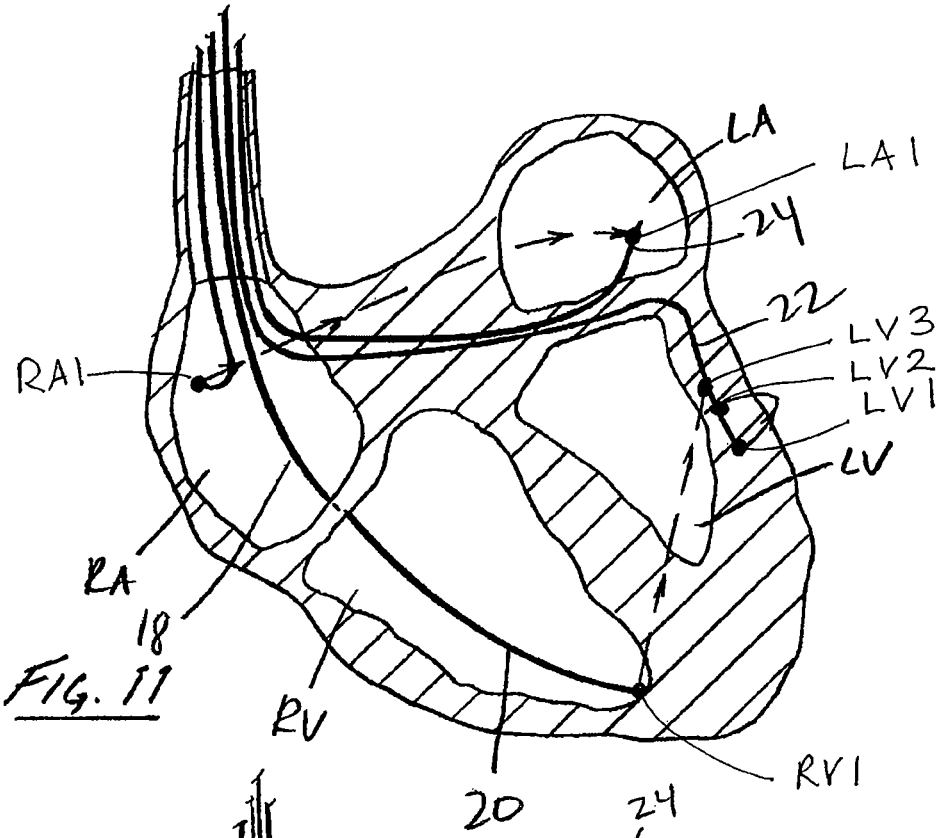
FIG. 11 is a schematic view showing the leads coupled to the heart and demonstrating the concept of four chamber pacing and multipolar LV pacing.

With reference now to FIG. 10, in one embodiment, the leads in the RA, RV, multipolar lead in the LV, and a LA lead are introduced via the vein of Marshall. With respect to FIG. 11, four chamber pacing and multipolar LV pacing are shown. LV1, LV4, and LV6 are paced by the LV channel. LV2 is the anode for LV1, and LV3 is the anode for RV. LA is the anode for the RA channel.

As noted previously, anodal pacing may be used to capture the His bundle or the very proximal right and left bundles, that is, His or Para-His pacing. By using a bipolar or multipolar lead, designed such that multiple poles are in contact with the tricuspid annulus in close proximity to the bundle of His, it should be possible to pace the selected structure (e.g. His Bundle) using the virtual cathode created by the fixed cathode; as well as the virtual cathode created by the anode(s). In this aspect of the invention, it will be important for the electrodes to be in close contact with the RV septum/TV annulus area.

A number of different embodiments are contemplated with respect to this aspect of the present invention. For instance, in one embodiment, a bipolar lead with an anode closely applied to the RV septum by a preformed bend or a screw may be utilized. In this case, if either the cathode or the anode lies in close proximity with the His bundle, capture by the virtual cathodes generated by the cathode and/or anode is likely to occur. If a large His potential is recorded between the cathode and the anode, His capture is likely.

In another embodiment, a multipolar lead with closely spaced electrodes, some of which may be fixated to the RV septum may be used. In this case, these may be paced in different configurations. That is, for example, the pacing may utilize some cathodes, some anodes, or summation anodes between the His cathodes, LV cathodes, and/or RV cathodes.

Anodal pacing may additional be used in patients requiring biatrial pacing. Such patients may have left atrial leads inserted transvenously via the obtuse vein of Marshall, surgically implanted, or introduced to the left atrium via different means. The right atrial lead would be placed in the right atrium in the conventional fashion. One of the leads' terminal electrodes would function as the cathode while the other would function as an anode. In another aspect of the invention, the left atrial lead serves as the anode for the RV pacing lead: Tthe RV is paced at least 70 msec after the RA; and a similar timing has been suggested for the LA (FIG. 13).

Studies have confirmed that an application having a common anode for more than one cathode has a lower stimulation threshold than a corresponding application having a single anode for each cathode. The study involved six human subjects undergoing pacemaker or defibrillator implantation. The inter-operative determination of the anodal threshold at a 0.5 millisecond pulse width was determined. The anodal threshold of each of the cathodes "a" and "b" were determined using a single anode for each of the cathodes and using the same anode for both cathodes.

The study confirmed that an anode serving as a common anode for two cathodes has a capture threshold that is half the sum of the anodal threshold obtained from each cathode alone.

This is particularly significant from a clinical standpoint. When multiple sites are paced simultaneously using multiple cathodes, an anode common to two or more cathodes will capture at lower cathodal pacing thresholds than an anode for a single cathode. As a result, the anodal current that would otherwise be wasted by returning to the device or to a lead anode not configured to provide pacing can be directed to an anode that can be used to pace another chamber or another segment of the same chamber.

In another study, a population of 100 patients undergoing biventricular ICD or pacemaker implantation was studied. The mean age of the 100 patients was 66+/−12 years. The study included 44 female patients. The mean left ventricular ejection fraction was 26+/−16%. The thresholds were measured in a number of configurations including bipolar, unipolar cathodal, and unipolar anodal. In the bipolar configuration, the thresholds were measured from the LV tip to the LV ring and the LV ring to the LV tip at varying impedances. In the unipolar, cathodal configuration, the thresholds were measured from the LV tip to the RV coil, the LV tip to the case, the LV ring to the RV coil, the LV ring to the case, the LV tip to the RA ring, and the LV ring to the RA ring. In the unipolar anodal configuration, the threshold was measured from the case to the LV tip, from the case to the LV ring, from the RV coil to the LV tip, and from the RV coil to the LV ring.

The mean measured LV threshold unipolar, cathodal from the LV tip was 1.7+/−1.7 while unipolar, anodal was 2.4+/−2.1. From the LV ring electrode, the unipolar cathodal threshold was 1.6+/−1.2 and the unipolar anodal threshold was 3.4+/−1.8. During single cathode LV pacing, anodal thresholds of <2.5 were obtained in ⅔ of patients using the tip electrode and in ⅓ of all patients using the ring electrode. The proportion of patients with adequate thresholds is expected to be considerably higher in summation anodal pacing. Thus, it is feasible to use the anodal current generated as a byproduct of cathodal pacing and use it for pacing another site in the left ventricle in >⅔ patients. This proportion is also expected to increase in using summation anodal pacing.

Although the best mode contemplated by the inventor of carrying out the present invention is disclosed above, practice of the present invention is not limited thereto. It will be manifest that various additions, modifications and rearrangements of the aspects and features of the present invention may be made in addition to those described above without deviating from the spirit and scope of the underlying inventive concept. The scope of some of these changes is discussed above. The scope of other changes to the described embodiments that fall within the present invention but that are not specifically discussed above will become apparent from the appended claims and other attachments.

I claim:

1. A device for applying an electrical current to a heart, the device comprising:

a current source;

a plurality of leads which are connected to the current source, wherein the leads include first, second, and third leads that are connectable to a right atrium of a heart, a right ventricle of the heart, and a left ventricle of the heart, respectively; wherein each of the leads has at least one electrode and at least one of the leads has at least two electrodes, wherein at least one of the electrodes serves as a cathode and at least one of the electrodes serves as an anode, wherein a surface area of at least one of the electrodes is sized sufficiently small to cause anodal capture, wherein the current source is controlled to deliver solely cathodal stimulation to at least one electrode, wherein at least one other electrode is a return electrode and the stimulation creates an area of hyper-polarization of the myocardial cell membrane and resultant modal capture of a portion of the heart via the return electrode, wherein the return electrode is a pacing electrode, and wherein cathodal stimulation is simultaneous with anodal capture that occurs solely as a consequence of the cathodal stimulation of another electrode.

2. The device of claim 1, wherein an anode receives current from at least two cathodes.

3. The device of claim 1, wherein the third lead includes one or more electrodes that serves as a cathode and one or more electrode that serves as the anode.

4. The device of claim 1, wherein the second lead includes a proximal electrode that is at least seven times the surface area of a tip electrode.

5. A method of cardiac pacing, the method comprising the steps of:

coupling first, second, and third leads to a right atrium of a heart, a right ventricle of a heart, and a left ventricle of the heart, respectively, wherein each of the leads has at least one electrode and at least one of the leads has at least two electrodes, and wherein at least one electrode serves as a cathode and at least one electrode serves as an anode; and delivering solely cathodal stimulus current to at least one electrode wherein at least one other electode is a return electrode and the stimulus current creates an area of depolarization of one part of the myocardial cell membrane and resultant cathodal stimulation and hyper-polarization of another part the myocardial cell membrane and resultant anodal capture of another portion of the heart via the return electrode, wherein the return electrode is a pacing electrode, wherein the cathodal stimulation and the anodal capture of the another portion of the heart are simultaneous, and wherein and the anodal capture occurs solely as a consequence of the cathodal stimulation of another electrode.

6. The method of claim 5, further comprising the steps of: coupling, a unipolar or bipolar lead to a left atrium; and delivering a stimulus current to the unipolar or bipolar lead from the current source.

7. The method of claim 5, wherein an anode of the third lead serves as the anode to two cathodes.

8. The method of claim 5, wherein the current is delivered to the first, second, and third leads at different times.

9. The method of claim 8, wherein the current is delivered to the second lead at least seventy milliseconds after delivering current to the first lead.

10. The method of claim 5, further comprising coupling a fourth lead to a left atrium of the heart, and wherein the stimulus current is a sub-threshold stimulus current is applied to the third lead simultaneously with and purely as a consequence of stimulation of one of the first and fourth leads.

11. The method of claim 5, wherein the third lead is multipolar and has at least three electrodes, and wherein the stimulus current is delivered to the electrodes of the third lead at different times.

12. A method of cardiac pacing, the method comprising the steps of:

coupling a first lead, a second lead, and a third lead to a right atrium of a heart, a right ventricle of the heart, and a left ventricle of the heart, respectively, wherein each of the leads has at least one electrode and at least one of the leads has a plurality of electrodes, and wherein at least one electrode serves as a cathode and at least one electrode serves as an anode; and applying a solely cathodal stimulus current to at least one electrode wherein at least one electrode is used as a return electrode and the stimulus current creates an area of hyper-polarization of the myocardial cell membrane and resultant modal capture of a portion of the heart via the return electrode, wherein the return electrode is a pacing electrode, wherein an anode of the third lead serves as the anode to two or more cathodes, and wherein anodal capture of the portion of the heart as a result of the stimulation occurs solely as a consequence of the cathodal stimulation of another electrode.

13. A method of cardiac pacing, the method comprising the steps of:

coupling a first lead, a second lead, and a third lead to a right atrium of a heart, a right ventricle of the heart, and a left ventricle of the heart, respectively, wherein each of the leads has at least one electrode and at least one of the leads has a plurality of electrodes, and wherein at least one electrode serves as a cathode and at least one electrode serves as an anode; and delivering solely cathodal stimulus current to at least one electrode wherein at least one other electrode is a return electrode and the stimulus creates an area of depolarization of one part of the myocardial cell membrane and resultant cathodal stimulation and hyper-polarization of another part the myocardial cell membrane and resultant anodal capture of a portion of the heart via return electrode, wherein the return electrode is a pacing electrode, wherein the cathodal stimulation and the anodal capture of the portion of the heart as a result of stimulation are simultaneous and the anodal capture occurs solely as a consequence of the cathodal stimulation of another electrode, and wherein the stimulus current is delivered to the electrodes at different times.

14. A method of cardiac pacing, the method comprising the steps of:

providing a device comprising:

a current source;

a plurality of leads which are connected to the current source, wherein each lead is connected to at least one of a right atrium of a heart, a right ventricle of the heart, a left atrium of the heart, and a left ventricle of the heart;

wherein at least one electrode is associated with each of the leads and at least two electrodes are associated with at least one of the leads, wherein at least one electrode serves as a cathode and at least one electrode serves as an anode, wherein an anodal surface area is sized to cause anodal capture; and delivering solely cathodal stimulus current to at least one electrode wherein at least one other electrode is a return electrode and the stimulus creates an area of depolarization of one part of the myocardial cell membrane and resultant cathodal stimulation and hyper-polarization of another part the myocardial cell membrane and resultant anodal capture of another portion of the heart via the return electrode, wherein the return electrode is a pacing electrode, wherein the cathodal stimulation and the anodal capture are simultaneous and the anodal capture of the another portion of the heart as a result of the stimulation occurs solely as a consequence of the cathodal stimulation of another electrode.

15. The method of claim 14, wherein at least two cathodes stimulate one anode.

16. The method of claim 14, wherein the lead that is connected to the left ventricle is multipolar and comprises a plurality of electrodes that serve as cathodes and a plurality of electrodes that serve as anodes.

17. The method of claim 14, wherein an electrode that is connected to the left ventricle serves as the anode for an electrode of the right ventricle and an electrode of the left ventricle both serving as cathodes.

18. The method of claim 14, wherein an electrode on the right ventricle serves as the anode for at least one electrode of the left ventricle serving as a cathode.

19. The method of claim 14, further comprising delivering current to the leads from the current source such that the left ventricle is stimulated earlier than the right ventricle, the electrodes of the left ventricle serving as cathodes are stimulated earlier than the electrodes of the left ventricle serving as anodes, and such that the electrodes of the left ventricle serving as anodes receive current from the electrodes of the right ventricle serving as cathodes.

20. The method of claim 14, further comprising delivering current to the leads from the current source such that the right ventricle is stimulated earlier than the left ventricle, the electrodes of the left ventricle serving as anodes are stimulated earlier than the electrodes of the left ventricle serving as cathodes, and such that the electrodes of the left ventricle serving as anodes receive current from the electrodes of the right ventricle serving as cathodes.

21. The method of claim 5, further comprising the step of inserting a fourth lead into a left atrium of the heart, and wherein anodal pacing is performed on the left atrium and the right atrium of the heart.

*22. A device for applying an electrical current to a heart, the device comprising:*

*a current source;*

*a plurality of leads which are connected to the current source,*

*wherein the leads include first, second, and third leads that are connectable to a right atrium of a heart, a right ventricle of the heart, and a left ventricle of the heart, respectively;*

*wherein each of the leads has at least one electrode and at least the third lead has at least two electrodes,*

*wherein at least one of the electrodes serves as a cathode and at least one of the electrodes serves as an anode,*

*wherein a surface area of at least one of the electrodes is sized sufficiently small to cause anodal capture,*

*wherein the current source is controlled to deliver solely cathodal stimulation to at least one electrode,*

*wherein at least one other electrode is a return electrode,*

*wherein the stimulation creates an area of hyperpolarization of the myocardial cell membrane and resultant anodal capture of a portion of the heart via the return electrode,*

*wherein the return electrode is a pacing electrode, and*

*wherein cathodal stimulation is simultaneous with anodal capture that occurs solely as a consequence of the cathodal stimulation of another electrode.*

*23. A device for applying an electrical current to a heart, the device comprising:*

*a current source;*

*a plurality of leads which are connected to the current source,*

*wherein the leads include first, second, and third leads that are connectable to a right atrium of a heart, a right ventricle of the heart, and a left ventricle of the heart, respectively;*

*wherein each of the leads has at least one electrode and the third lead has at least four electrodes,*

*wherein at least one of the electrodes serves as a cathode and at least one of the electrodes serves as an anode,*

*wherein a surface area of at least one of the electrodes is sized sufficiently small to cause anodal capture,*

*wherein the current source is controlled to deliver solely cathodal stimulation to at least one electrode,*

*wherein at least one other electrode is a return electrode,*

*wherein the stimulation creates an area of hyperpolarization of the myocardial cell membrane and resultant anodal capture of a portion of the heart via the return electrode,*

*wherein the return electrode is a pacing electrode, and*

*wherein cathodal stimulation is simultaneous with anodal capture that occurs solely as a consequence of the cathodal stimulation of another electrode.*

*24. The device of claim 23, wherein the third lead is a quadripolar lead having four electrodes.*

*25. The device of claim 24, wherein two of the electrodes on the quadripolar lead serve as anodes and two of the electrodes on the quadripolar lead serve as cathodes.*

*26. The device of claim 23, wherein an electrode on the second lead and two of the electrodes on the third lead serve as cathodes, and wherein one of the electrodes on the third lead serves as a common anode for a cathode on the second lead and two cathodes on the third lead.*

*27. The device of claim 23, wherein the second lead is a bipolar lead having a proximal electrode and a tip electrode, and wherein the proximal electrode has a surface area that is at least 7 times a surface area of the tip electrode.*

*28. A device for applying an electrical current to a heart, the device comprising:*

*a current source;*

*a plurality of leads which are connected to the current source,*

*wherein the leads include first, second, and third leads that are connectable to a right atrium of a heart, a right ventricle of the heart, and a left ventricle of the heart, respectively;*

*wherein each of the leads has at least one electrode and the third lead has at least four electrodes,*

*wherein at least one of the electrodes serves as a cathode and at least one of the electrodes serves as an anode,*

*wherein a surface area of at least one of the electrodes is sized sufficiently small to cause anodal capture,*

*wherein the current source is controlled to deliver solely cathodal stimulation to at least one electrode,*

*wherein at least one other electrode is a return electrode,*

*wherein the stimulation creates an area of hyper-polarization of the myocardial cell membrane and resultant anodal capture of a portion of the heart via the return electrode,*

*wherein the return electrode is a pacing electrode,*

*wherein cathodal stimulation is simultaneous with anodal capture that occurs solely as a consequence of the cathodal stimulation of another electrode,*

*wherein the third lead is a quadripolar lead having four electrodes,*

*wherein at least one electrode of the third lead serves as a cathode and at least one electrode of the third lead serves as an anode,*

*wherein the second lead is a bipolar lead having a proximal electrode and a tip electrode, and*

*wherein the proximal electrode on the bipolar lead has a surface area that is at least 7 times a surface area of the tip electrode on the bipolar lead.*

*29. A method of cardiac pacing, the method comprising the steps of:*

*coupling first, second, and third leads to a right atrium of a heart, a right ventricle of a heart, and a left ventricle of the heart, respectively, wherein each of the first and second leads has at least one electrode and at the third lead has at least two electrodes;*

*delivering solely cathodal stimulus current to at least one electrode wherein at least one other electrode is a return electrode and the stimulus creates an area of depolarization of one part of the myocardial cell membrane and resultant cathodal stimulation and hyperpolarization of another part the myocardial cell membrane and resultant anodal capture of a portion of the heart via the return electrode, wherein the return electrode is a pacing electrode, wherein the cathodal stimulation and the anodal capture of the portion of the heart as a result of stimulation are simultaneous and the anodal capture occurs solely as a consequence of the cathodal stimulation of another electrode, and wherein the stimulus current is delivered to the electrodes at different times.*

*30. The method of claim 29, wherein the third lead is a quadripolar lead having four electrodes.*

*31. A method of cardiac pacing, the method comprising the steps of:*

*providing a device comprising:*

*a current source;*

*a plurality of leads which are connected to the current source, wherein each lead is connected to at least one of a right atrium of a heart, a right ventricle of the heart, a left atrium of the heart, and a left ventricle of the heart, wherein each of the first and second leads has at least one electrode and the third lead has at least four electrodes;*

*wherein at least one electrode is associated with each of the leads and at least two electrodes are associated with at least one of the leads, wherein at least one electrode serves as a cathode and at least one electrode serves as an anode,*

*wherein an anodal surface area is sized to cause anodal capture; and*

*delivering solely cathodal stimulus current to at least one electrode wherein at least one other electrode is a return electrode and the stimulus creates an area of depolarization of one part of the myocardial cell membrane and resultant cathodal stimulation and hyperpolarization of another part the myocardial cell membrane and resultant anodal capture of another portion of the heart via the return electrode, wherein the return electrode is a pacing electrode, wherein the cathodal stimulation and the anodal capture are simultaneous and the anodal capture of the another portion of the heart as a result of the stimulation occurs solely as a consequence of the cathodal stimulation of another electrode.*

*32. The method of claim 31, wherein the third lead is a quadripolar lead having four electrodes.*

* * * * *